(12) United States Patent
Donohoe

(10) Patent No.: US 9,038,880 B1
(45) Date of Patent: May 26, 2015

(54) ARTICULATED SURGICAL INSTRUMENT

(75) Inventor: Brendan M. Donohoe, Fairfax, CA (US)

(73) Assignee: Cardica, Inc., Redwood City, CA (US)

( * ) Notice: Subject to any disclaimer, the term of this patent is extended or adjusted under 35 U.S.C. 154(b) by 627 days.

(21) Appl. No.: 13/093,743

(22) Filed: Apr. 25, 2011

(51) Int. Cl.
*A61B 17/072* (2006.01)
*A61B 1/00* (2006.01)

(52) U.S. Cl.
CPC .................................. *A61B 1/00064* (2013.01)

(58) Field of Classification Search
CPC .... A61B 1/005; A61B 1/0051; A61B 1/0055; A61B 2017/003; A61B 2017/00305; A61B 2017/00314; A61B 2017/00318; A61B 2017/00323; A61B 2017/00327; A61B 2017/2908; A61B 19/22
USPC ....................................... 227/175.1, 179.1, 19
See application file for complete search history.

(56) References Cited

U.S. PATENT DOCUMENTS

| | | | |
|---|---|---|---|
| 2,515,366 A | 7/1950 | Zublin | |
| 3,191,455 A | 6/1965 | Fuqua et al. | |
| D210,021 S | 1/1968 | Prifogie | |
| 3,497,608 A | 2/1970 | Elliott | |
| 3,557,780 A * | 1/1971 | Sato | 600/141 |
| 3,581,551 A | 6/1971 | Wilkinson | |
| 3,583,393 A | 6/1971 | Takahashi | |
| 3,650,453 A | 3/1972 | Smith, Jr. | |
| 3,837,555 A | 9/1974 | Green | |
| 3,899,914 A | 8/1975 | Akiyama | |
| 3,986,765 A | 10/1976 | Shaffer | |
| 4,086,926 A | 5/1978 | Green et al. | |
| 4,127,227 A | 11/1978 | Green | |
| 4,228,895 A | 10/1980 | Larkin | |
| 4,328,839 A | 5/1982 | Lyons et al. | |
| 4,475,679 A | 10/1984 | Fleury, Jr. | |
| 4,580,551 A * | 4/1986 | Siegmund et al. | 600/139 |
| 4,589,416 A | 5/1986 | Green | |
| 4,600,037 A | 7/1986 | Hatten | |
| 4,633,861 A | 1/1987 | Chow et al. | |
| 4,651,718 A * | 3/1987 | Collins et al. | 600/142 |
| 4,762,260 A | 8/1988 | Richards et al. | |
| 4,869,414 A | 9/1989 | Green et al. | |
| 4,969,591 A | 11/1990 | Richards et al. | |
| 5,042,707 A | 8/1991 | Taheri | |
| 5,143,475 A | 9/1992 | Chikama | |

(Continued)

FOREIGN PATENT DOCUMENTS

EP 1238634 9/1994
JP 2005160933 6/2005

(Continued)

OTHER PUBLICATIONS

Gong, Shao W., "Perfectly flexible mechanism and integrated mechanism system design", *Mechanism and Machine Theory* 39 (2004), (Nov. 2004),1155-1174.

(Continued)

*Primary Examiner* — Andrew M Tecco
(74) *Attorney, Agent, or Firm* — Cardica, Inc.

(57) ABSTRACT

An exemplary surgical apparatus may include a shaft defining a lumen therein; articulation bands extending through and slidable generally longitudinally within the lumen of the shaft; an end effector affixed to the articulation bands; and generally annular segments positioned about the articulation bands along at least a portion of the length of the articulation bands to define an articulated region, where the segments laterally constrain the articulation bands.

14 Claims, 8 Drawing Sheets

(56) References Cited

U.S. PATENT DOCUMENTS

| | | | |
|---|---|---|---|
| 5,156,315 A | 10/1992 | Green et al. | |
| 5,178,129 A * | 1/1993 | Chikama et al. | 600/142 |
| 5,192,288 A | 3/1993 | Thompson et al. | |
| 5,271,381 A * | 12/1993 | Ailinger et al. | 600/128 |
| 5,271,543 A | 12/1993 | Grant et al. | |
| 5,340,330 A | 8/1994 | Dolson et al. | |
| 5,381,943 A | 1/1995 | Allen et al. | |
| 5,405,073 A | 4/1995 | Porter | |
| 5,413,272 A | 5/1995 | Green et al. | |
| 5,448,989 A * | 9/1995 | Heckele | 600/142 |
| 5,456,400 A | 10/1995 | Shichman et al. | |
| 5,476,206 A | 12/1995 | Green et al. | |
| 5,485,952 A | 1/1996 | Fontayne | |
| 5,580,067 A | 12/1996 | Hamblin et al. | |
| 5,655,698 A | 8/1997 | Yoon | |
| 5,662,260 A | 9/1997 | Yoon | |
| 5,673,840 A | 10/1997 | Schulze et al. | |
| 5,692,668 A | 12/1997 | Schulze et al. | |
| 5,704,534 A * | 1/1998 | Huitema et al. | 227/175.1 |
| 5,749,828 A * | 5/1998 | Solomon et al. | 600/141 |
| 5,772,578 A | 6/1998 | Heimberger et al. | |
| 5,807,241 A | 9/1998 | Heimberger | |
| 5,810,855 A | 9/1998 | Rayburn et al. | |
| 5,816,471 A | 10/1998 | Plyley et al. | |
| 5,823,066 A | 10/1998 | Huitema et al. | |
| 5,855,311 A | 1/1999 | Hamblin et al. | |
| 5,857,964 A | 1/1999 | Konstorum et al. | |
| 5,894,979 A | 4/1999 | Powell | |
| 5,918,791 A | 7/1999 | Sorrentino et al. | |
| 5,964,774 A | 10/1999 | McKean et al. | |
| 6,053,922 A | 4/2000 | Krause et al. | |
| 6,306,149 B1 | 10/2001 | Meade | |
| 6,364,828 B1 * | 4/2002 | Yeung et al. | 600/142 |
| 6,391,038 B2 | 5/2002 | Vargas et al. | |
| 6,431,904 B1 | 8/2002 | Berelsman | |
| 6,602,252 B2 | 8/2003 | Mollenauer | |
| 6,656,195 B2 | 12/2003 | Peters et al. | |
| 6,716,232 B1 | 4/2004 | Vidal et al. | |
| 6,755,338 B2 | 6/2004 | Hahnen et al. | |
| 6,786,382 B1 | 9/2004 | Hoffman | |
| 6,817,508 B1 | 11/2004 | Racenet et al. | |
| 6,827,601 B1 | 12/2004 | Haeberle | |
| 6,843,403 B2 | 1/2005 | Whitman | |
| 7,025,747 B2 | 4/2006 | Smith | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 * | 5/2007 | Wales et al. | 227/180.1 |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,300,297 B1 | 11/2007 | Wang et al. | |
| 7,316,575 B2 | 1/2008 | Muschketat et al. | |
| 7,407,077 B2 | 8/2008 | Ortiz et al. | |
| 7,434,716 B2 | 10/2008 | Viola | |
| 7,486,994 B2 | 2/2009 | Zarembo et al. | |
| 7,506,790 B2 * | 3/2009 | Shelton, IV | 227/176.1 |
| 7,507,109 B2 | 3/2009 | Tran | |
| 7,575,144 B2 | 8/2009 | Ortiz et al. | |
| 7,617,961 B2 * | 11/2009 | Viola | 227/175.1 |
| 7,654,838 B1 | 2/2010 | Zhuge | |
| 7,670,334 B2 | 3/2010 | Hueil et al. | |
| 7,682,319 B2 * | 3/2010 | Martin et al. | 600/585 |
| 7,708,182 B2 | 5/2010 | Viola | |
| 7,819,298 B2 | 10/2010 | Hall et al. | |
| 7,828,808 B2 * | 11/2010 | Hinman et al. | 606/108 |
| 8,123,703 B2 * | 2/2012 | Martin et al. | 600/585 |
| 8,236,010 B2 * | 8/2012 | Ortiz et al. | 606/142 |
| 8,287,469 B2 * | 10/2012 | Stefanchik et al. | 600/585 |
| 8,317,074 B2 * | 11/2012 | Ortiz et al. | 227/176.1 |
| 8,419,747 B2 * | 4/2013 | Hinman et al. | 606/108 |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2005/0272978 A1 | 12/2005 | Brunnen et al. | |
| 2005/0273084 A1 * | 12/2005 | Hinman et al. | 606/1 |
| 2006/0011699 A1 | 1/2006 | Olson et al. | |
| 2006/0025811 A1 * | 2/2006 | Shelton | 606/205 |
| 2006/0041273 A1 | 2/2006 | Ortiz et al. | |
| 2006/0047307 A1 | 3/2006 | Ortiz et al. | |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |
| 2007/0161860 A1 * | 7/2007 | Hosoi et al. | 600/142 |
| 2007/0175947 A1 | 8/2007 | Ortiz et al. | |
| 2007/0221700 A1 * | 9/2007 | Ortiz et al. | 227/175.1 |
| 2007/0221701 A1 | 9/2007 | Ortiz et al. | |
| 2008/0249364 A1 | 10/2008 | Korner | |
| 2008/0257935 A1 | 10/2008 | Viola | |
| 2009/0065552 A1 * | 3/2009 | Knodel et al. | 227/180.1 |
| 2009/0076506 A1 | 3/2009 | Baker | |
| 2009/0090764 A1 | 4/2009 | Viola | |
| 2009/0099420 A1 * | 4/2009 | Woodley et al. | 600/142 |
| 2009/0177041 A1 | 7/2009 | Stefanchik et al. | 600/146 |
| 2009/0198105 A1 * | 8/2009 | Sugisawa | 600/156 |

FOREIGN PATENT DOCUMENTS

| | | |
|---|---|---|
| RU | 2080833 | 6/1997 |
| WO | WO-81/01953 | 7/1981 |
| WO | WO-85/01427 | 4/1985 |
| WO | WO2004/103430 | 12/2004 |

OTHER PUBLICATIONS

Lim, Jonas J., et al., "A review of mechanism used in laparascopic surgical instruments", *Mechanism and Machine Theory* 38, (2003),1133-1147.

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

"Cardica Microcutter Implant Delivery Device 510(k), Cover Sheet, Table 10.1, Substantial Equivalence Comparison," and Section 12, "Substantial Equivalence Discussion", dated 2010.

\* cited by examiner

US 9,038,880 B1

ARTICULATED SURGICAL INSTRUMENT

FIELD OF THE INVENTION

The invention generally relates to the articulation of a surgical instrument.

BACKGROUND

Minimally invasive surgery is performed through small incisions in the body, into which trocar ports may or may not be placed. One or more surgical instruments are inserted through each incision in order to perform the surgical procedure. In order to effectuate one of the objectives of minimally invasive surgery, which is the minimization of incisions to the body to reduce healing time and scarring, it is desirable to minimize the number of incisions made in the body. The number of incisions and their placement are determined by the particular surgical procedure to be performed and the configuration of the instruments used to carry out that procedure.

One problem encountering during the performance of a minimally invasive surgical procedure is access to the tissue to be treated. Depending on the specific anatomy of the patient, it may be difficult to reach an area to be treated with a specific surgical instrument. As a result, one or more additional incisions may need to be made in the patient in order to access that tissue. The surgeon may need to obtain a different surgical instrument, adding to the time and expense of the procedure. Additionally, where more incisions may be made or additional instruments may be utilized, it can be difficult and/or time-consuming for the surgeon to find the surgical site again.

BRIEF DESCRIPTION OF THE DRAWINGS

The use of the same reference symbols in different figures indicates similar or identical items.

DETAILED DESCRIPTION

U.S. Patent Application Publication Ser. No. 2009/0065552, published on Mar. 12, 2009, and U.S. patent application Ser. No. 12/400,760, filed on Mar. 9, 2009, (the "Reference Documents") are hereby incorporated by reference herein in their entirety.

Figure 1:
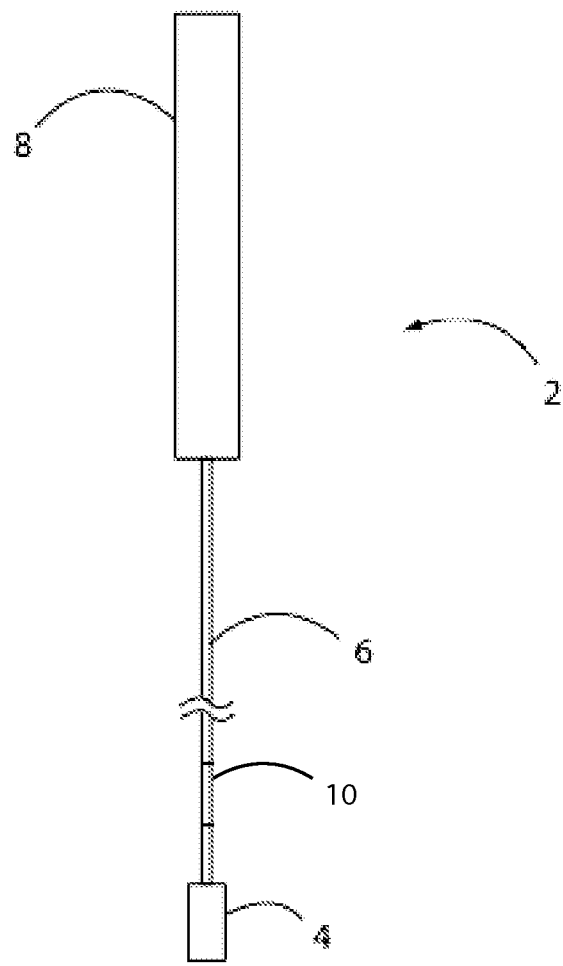
FIG. 1 is a schematic view of an exemplary surgical instrument.

Referring to FIG. 1, an surgical instrument 2 such as an endocutter may include an end effector 4 attached to a shaft 6, which in turn is attached to a handle 8. The end effector 4 may be one or more separate components that are connected to the shaft 6, or may be fabricated integrally with the distal end of the shaft 6. The shaft 6 of the surgical instrument 2 extends distally from the handle 8. The shaft 6 may be flexible or rigid, in whole or in part. The handle 8 may be attached to the proximal end of the shaft 6, or any other suitable portion of the shaft 6. The shaft 6 may be fabricated integrally with the handle 8. Alternately, the shaft 6 and the handle 8 may be two separate items that are connected together in any suitable manner. The handle 8 may include any mechanism, mechanisms, structure or structures that are suitably configured to actuate the end effector 4. The handle 8 may also include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in the U.S. patent application Ser. No. 11/054,265, filed on Feb. 9, 2005, which is herein incorporated by reference in its entirety. The handle 8 may instead, or also, include a connector or connectors suitable for receiving stored energy from an external source, such as a hose connected to a hospital utility source of pressurized gas or of vacuum, or an electrical cord connectable to a power source. An articulation region 10 extends distally from the shaft 6, and contacts the end effector 4. In this way, the end effector 4 is longitudinally spaced apart from the shaft 6.

Figure 2:
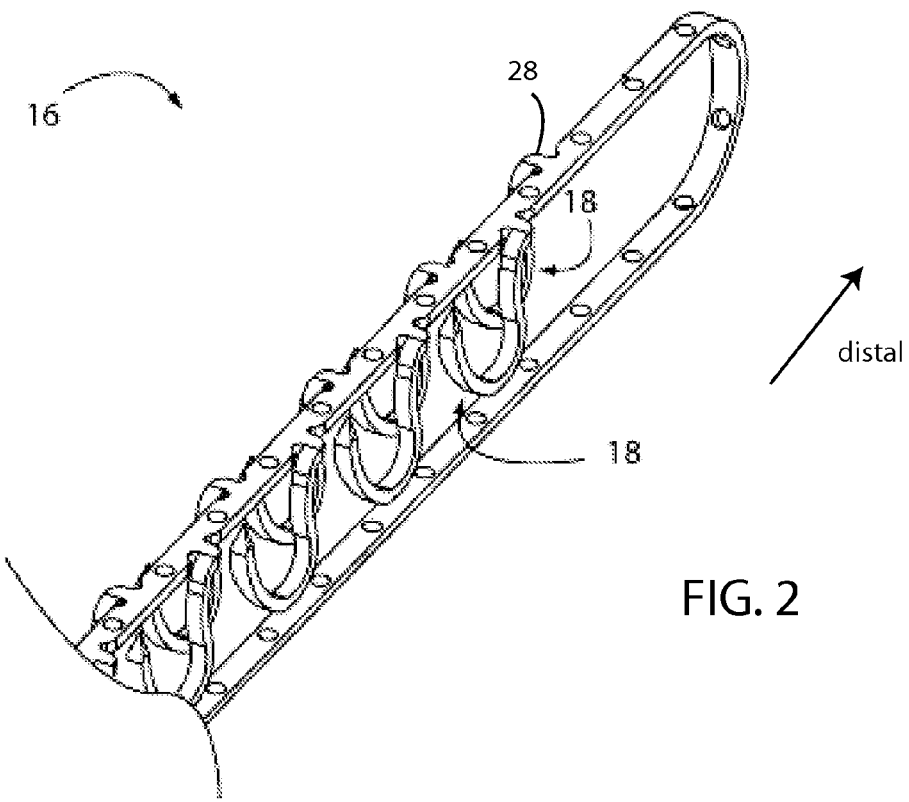
FIG. 2 is a perspective view of a feeder belt with staples affixed thereto.

Referring to FIG. 2, a portion of a feeder belt 16 is positioned within the end effector 4. The feeder belt 16 extends from the end effector 4 proximally through the articulation region 10, the shaft 6, and into the handle 8. The feeder belt 16, and its placement in a surgical instrument 2, may be substantially as set forth in the Reference Documents. The feeder belt 16 may be a long, narrow, thin strip of material from which one or more staples 18 extend. The feeder belt 16 may be fabricated from stainless steel, nickel-titanium alloy, or any other suitable metallic or non-metallic material. The feeder belt 16 is flexible enough, and strong enough, to be advanced linearly and then redirected around a nose or other structure in substantially the opposite direction, as described in greater detail below. Alternately, the feeder belt 16 may be rigid or at least partially rigid, and may be advanced or retracted substantially linearly without redirection about a structure. Each staple 18 may be shaped in any suitable manner; the staples 18 may be shaped substantially the same as one another, or may be shaped differently.

Figure 3:
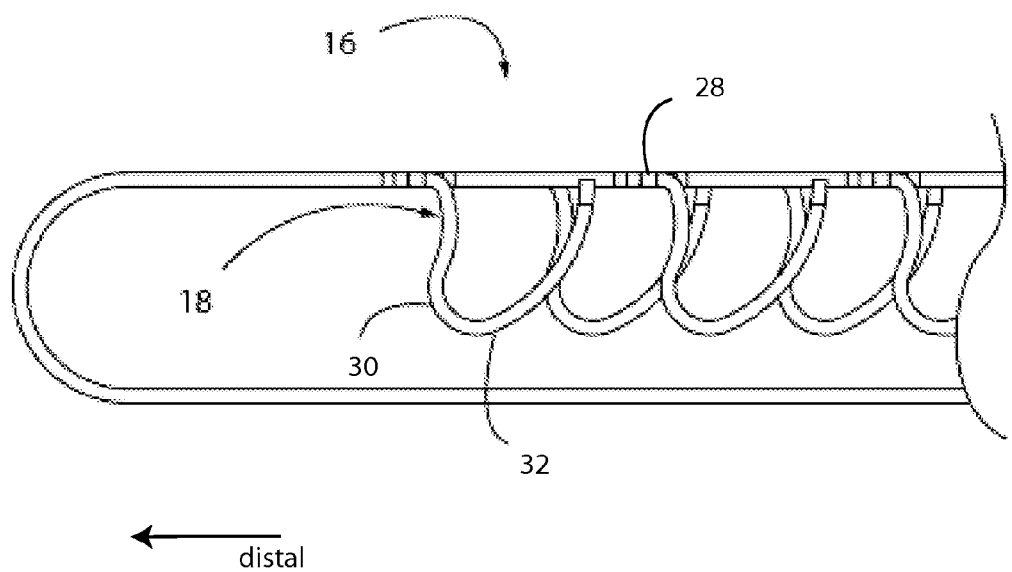
FIG. 3 is a side view of the feeder belt of FIG. 2.

As one example, at least one staple 18 may be shaped as a continuous curve, as may be most clearly seen in FIGS. 2-3. One end of the staple 18 may be connected to the feeder belt 16, such as via a tab 28 included in and protruding laterally from the feeder belt 16, as described in greater detail below. Alternately, the tab 28 is not utilized. The staple 18 may extend proximally and downward from the feeder belt 16. Then, the staple 18 may continue to curve downward, but also curve distally to form a bump 30. This bump 30 may extend to the longitudinal position of the tab 28, further distally than the longitudinal position of the tab 28, or not as far longitudinally as the tab 28. Then, the staple 18 may continue to curve downward, but also curve proximally. The staple 18 continues to curve proximally, then begins to curve upward at an inflection point 32. The staple 18 then continues to curve upward and proximally until terminating at a free end 22 at its proximal end. Alternately, the staple 18 may be oriented in the opposite direction, such that it extends distally and downward from the feeder belt 16.

The feeder belt 16 and staples 18 may be fabricated in any suitable manner. As one example, a flat, thin sheet of material is laser cut into long strips, after which each strip is laser cut or stamped to form fingers therein that are then bent into the shape of the staples 18. In this way, the staples 18 and the feeder belt 16 form an integral structure. However, the feeder belt 16 and staples 18 may be fabricated in any other suitable manner. As one example, the staples 18 and feeder belt are fabricated separately, and the staples 18 are then connected to the feeder belt 16 by welding, adhesive, or any other method that provides a frangible connection between the staples 18 and the feeder belt 16.

A frangible connection between the feeder belt 16 and each corresponding staple 18 may be made in any suitable manner. As one example, referring particularly to FIG. 6, each feeder belt 16 may include at least one tab 28 protruding laterally therefrom, or defined laterally in the center thereof. Alternately, at least one tab 28 may be oriented differently. Advantageously, the tabs 28 result from laser cutting and subsequent mechanical deformation of the staples 18 during manufacturing, such that the tabs 28 and staples 18 are integral with the corresponding feeder belt 16. However, the tabs 28 and/or staples 18 may be fabricated and connected to the feeder belt 16 in any other suitable manner. At least one staple 18 may be attached to a corresponding tab 28 in any suitable manner. The attachment between a staple 18 and the corresponding tab 28 may be made in any suitable manner, and the connection between a staple 18 and the corresponding tab 28 may have any suitable orientation. As one example, at least one tab 28 is generally rectangular, and the corresponding staple 18 extends from the proximal edge of that rectangular tab 28. The staple 18 may be separable from the tab 28, at a location generally at the intersection between the staple 18 and the tab 28. The connection between a staple 18 and the corresponding tab 28 is strong enough to hold the staple 18 securely in place relative to the feeder belt 16 prior to deployment, and weak enough to be broken or otherwise separated from the tab 28 during or after deployment. Alternately, the staple 18 is directly affixed to the feeder belt 16 without the use of a tab 28. Optionally, a staple 18, portion of the feeder belt 16, and/or tab 28 may include a weakened area at or near their intersection, in order to facilitate separation between the staple 18 and the feeder belt 16 during or after deployment. The weakened area may have a reduced cross-sectional area, may be notched, or otherwise structurally weakened. Alternately, the weakened area may also, or instead, be physically treated or otherwise configured to be weaker than the surrounding material, while having substantially the same physical dimensions as that surrounding material.

Figure 6:
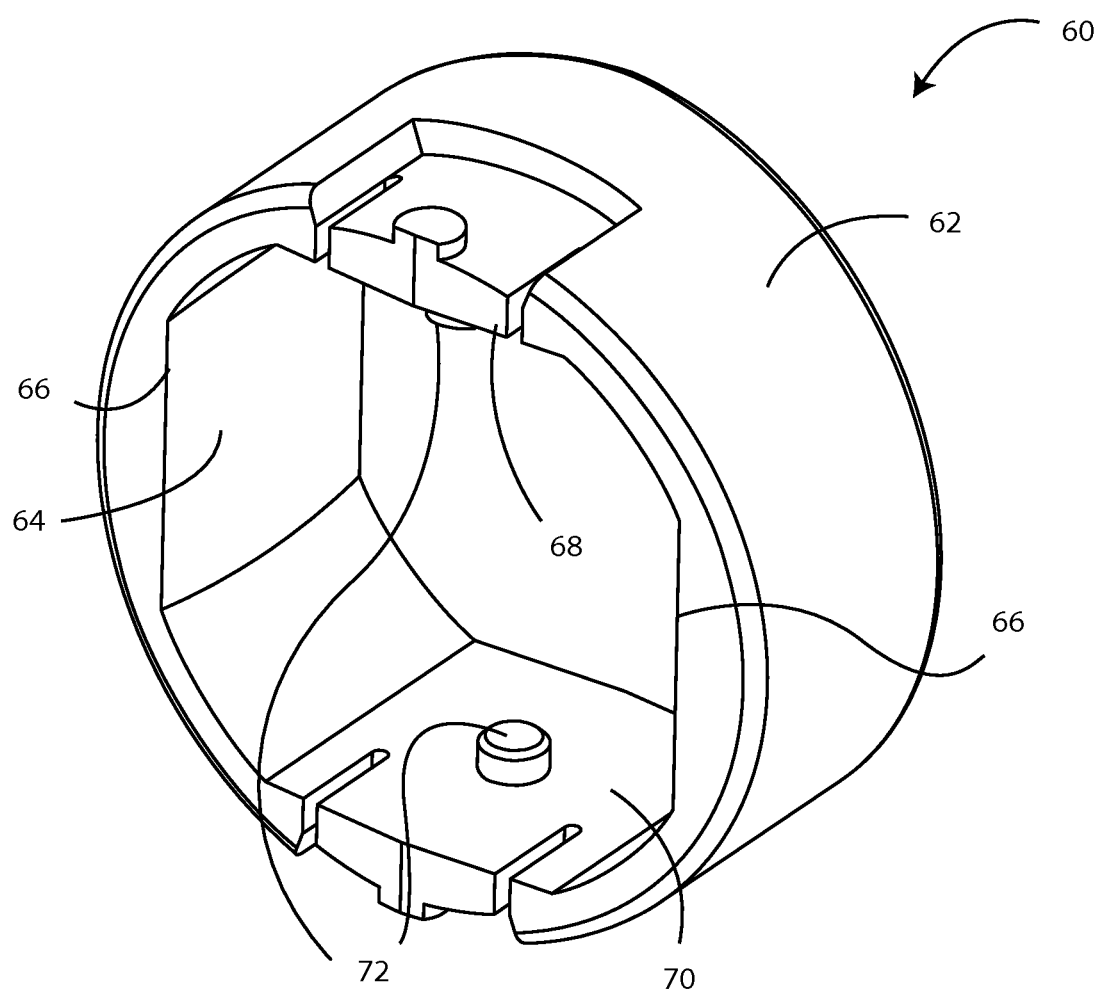
FIG. 6 is a perspective view of a segment of the articulation region of the surgical instrument of FIG. 5.

The staples 18 are in an initial configuration prior to being deployed. In the initial configuration, the staples 18 do not substantially contact one another. Alternately, at least two of the staples 18 may contact one another in the initial configuration. The staples 18 each may lie substantially in a single plane. That is, the staple 18 may be shaped such that a single plane extends through and substantially bisects the staple 18. Alternately, at least one staple 18 does not lie substantially in a single plane. At least one staple 18 may be positioned in a plane that is generally perpendicular to the feeder belt 16. Alternately, at least one staple 18 may be positioned in a plane that is angled differently relative to the feeder belt 16. One or more rows 26 of staples 18 are connected to the feeder belt 16. Each row 26 of staples 18 is the group of staples 18 positioned at substantially the same lateral location relative to the longitudinal centerline of the feeder belt 16, and each row 26 of staples 18 is oriented generally longitudinally. As best seen in FIG. 6, three rows 26 of staples 18 may be attached to the feeder belt 16—one row 26 along each side of the feeder belt 16, and one row 26 along the center of the feeder belt 16. The feeder belt 16 may form a continuous loop, or may have a discrete beginning and end that are not attached to one another. Alternately, more or fewer rows 26 of staples 18 may be attached to the feeder belt 16. Each row 26 may extend along part, or all, or the length of the feeder belt 16. Different rows 26 may extend different lengths along the feeder belt 16.

Figure 4:
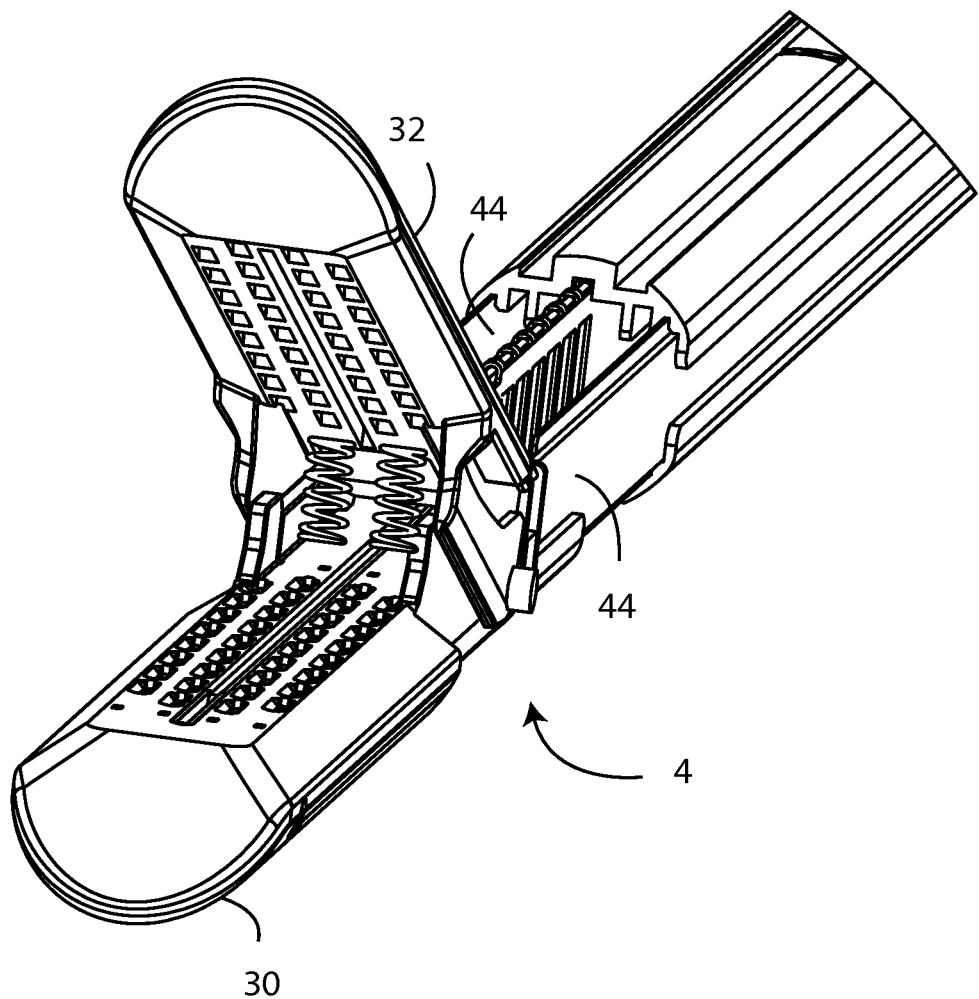
FIG. 4 is a perspective view of an exemplary end effector of the surgical instrument of FIG. 1.

Referring also to FIG. 4, the end effector 4 may include a staple holder 30 and an anvil 32. The anvil 32 may be movable relative to the staple holder 30 to compress tissue therebetween. The anvil 32 may include standard staple bending features defined therein to facilitate closure of the staples 18. Alternately, staple bending features may be omitted from the anvil 32. Advantageously, the staple holder 30 is fixed to a remainder of the end effector 4 and/or the shaft 6, and is not detachable therefrom. The staple holder 30 and anvil 32 may be configured as set forth in the Reference Documents. Alternately, the end effector 4 may be configured in any other manner for treatment of the body, and need not include a staple holder 30 or deploy staples 18.

Figure 5:
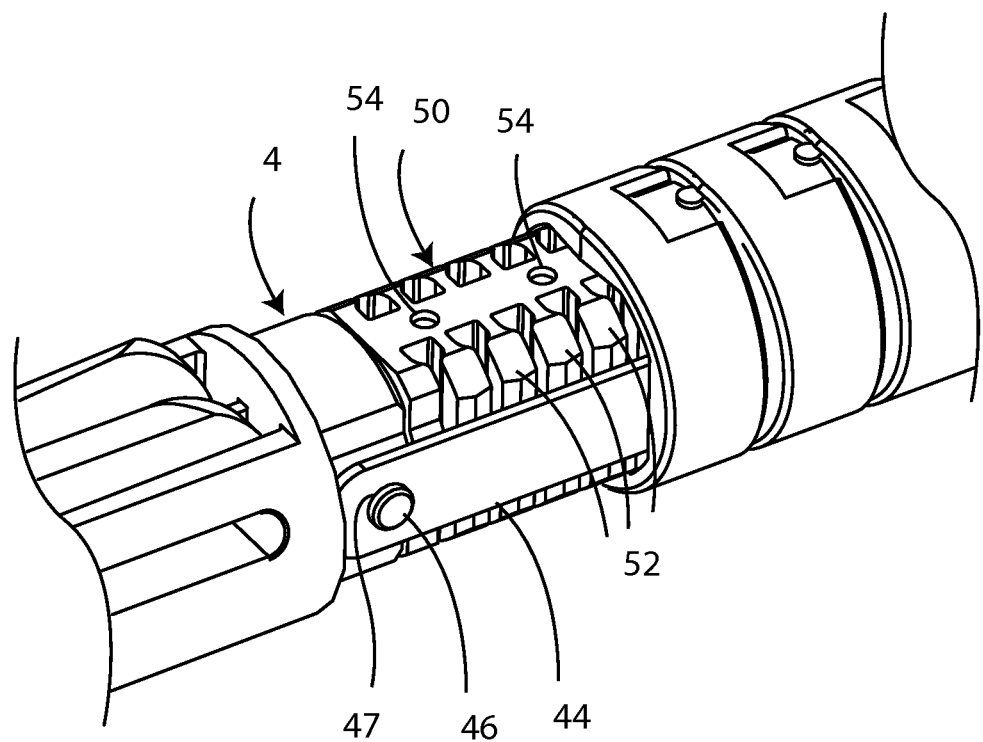
FIG. 5 is a perspective cutaway view of an articulation region of the surgical instrument of FIG. 1.

Referring to FIGS. 4-5, one or more articulation bands 44 extend proximally from the end effector 4 through the articulation region 10 and the shaft 6 to the handle 8. The articulation bands 44 may be generally rectangular in cross section, where the bands 44 may be significantly greater in the height dimension than in the lateral dimension. In this way, the articulation bands 44 have a suitably low moment of inertia to allow lateral flexing of the articulation region 10. Alternately, the articulation bands 44 may have any other suitable cross-section, and such cross-section need not be constant along the length of either articulation band 44. Further, the articulation bands 44 may be composed of a material such as spring steel that allows the articulation bands 44 to provide resistance to compressive force. Each articulation band 44 may be fixed at or near its distal end to the end effector 4. As one example, at least one articulation band 44 may include an aperture 47 defined therethrough that is placed over a corresponding pin 46 included in the end effector 4. The pin 46 may be a pin about which the anvil 32 pivots relative to the staple holder 30. Alternately, the pin 46 may simply hold the corresponding articulation band 44. Alternately, at least one articulation band 44 may be fixed to the end effector 4 by welding, adhesive, or any other suitable connection. Each articulation band 44 may extend to a different lateral side of the end effector 4. Alternately, at least one articulation band 44 may be oriented relative to the end effector 4.

A central core 50 may be located proximal to the end effector 4. The central core 50 may be fixed to the end effector 4, such as at or near the proximal end of the end effector 4. As another example, the central core 50 may be compressed between the end effector 4 and the shaft 6 or a fitting in the shaft 6 proximal to the articulation region 10. The central core 50 may extend into and/or completely through the articulation region 10. Consequently, at least the portion of the central core 50 that is located in the articulation region 10 is flexible and/or bendable. As one example, at least the portion of the central core 50 located in the articulation region 10 may be composed of a flexible material, such as but not limited to silicone or elastomer. This flexible material may be resilient, meaning that it tends to return to a neutral state after deflection, or nonresilient, meaning that it tends to remain in a deflected state after deflection. As another example, at least the portion of the central core 50 located in the articulation region 10 may include core segments 52, where at least part of each core segment 52 is spaced longitudinally apart from at least one adjacent segment. Those core segments 52 may be individually rigid or flexible; the spacing between the core segments 52 allows the portion of the central core 50 that may be composed of such core segments 52 to bend. As another example, the central core 50 may be the articulation insert described in U.S. patent application Ser. No. 12/436,087, filed on May 5, 2009 or U.S. patent application Ser. No. 12/477,065, filed on Jun. 2, 2009 (collectively referred to as the "Insert Documents"), both of which are herein incorporated by reference in their entirety. At least one pin receiver 54 may be defined in the central core 50. Advantageously, several pin receivers 54 may be defined in an upper surface of the central core 50, and several may be defined also in a lower surface of the central core 50.

Referring also to FIG. 6, the articulated region 10 may include one or more segments 60. Each segment 60 may be generally annular. The outer surface 62 of each segment 60 may be generally cylindrical, and the inner surface 64 may have two lateral walls 66 that are each substantially vertical, and substantially parallel to one another. The upper wall 68 and lower wall 70 of the inner surface 64 may be substantially horizontal and substantially parallel to one another. Alternately, the inner surface 64 and/or outer surface 62 of one or more segments 60 may have any suitable shape. The lateral walls 66 may be at least as high as the articulation bands 44. At least one pin 72 may extend from the inner surface 64 of a segment 60, advantageously toward the longitudinal centerline of the segment 60. At least one segment 60 may be plastic, such as injection-molded plastic.

Figure 7:
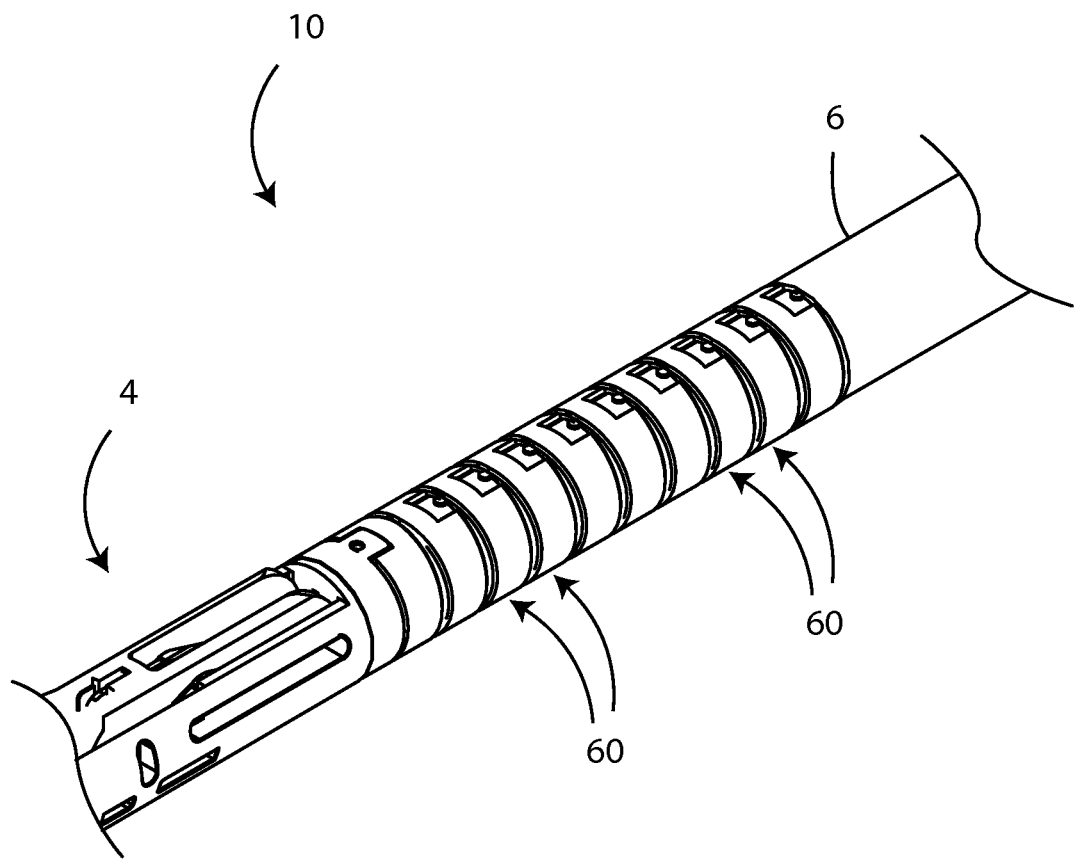
FIG. 7 is a perspective view of the articulation region of FIG. 6, in a neutral, non-articulated configuration.
Figure 8:
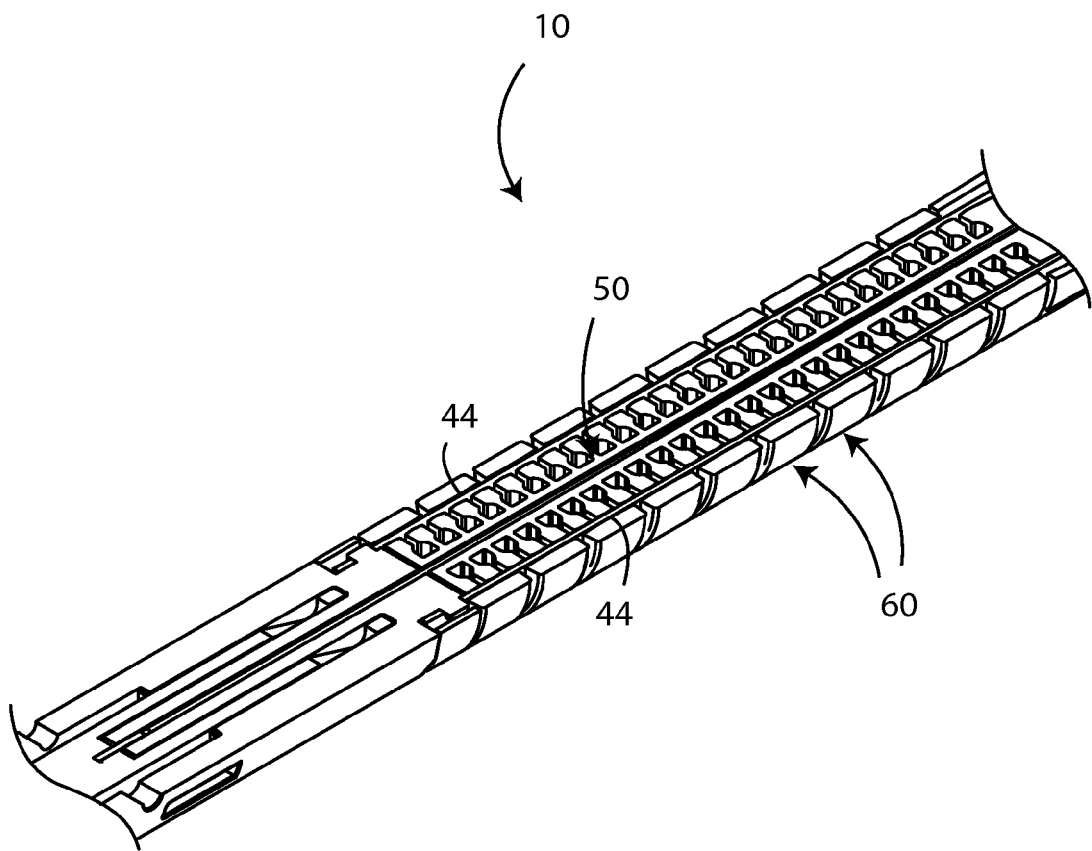
FIG. 8 is a perspective cross-section view of FIG. 7.

At least one such pin 72 is received in a corresponding pin receiver 54 of the central core 50. Advantageously, one pin 72 of each segment 60 is received in a pin receiver 54 in the upper surface of the central core 50, and another pin 72 of each segment 60 is received in a pin receiver 54 in the lower surface of the central core 50, such that the pins 72 align along an axis about which the segment 60 can pivot relative to the central core 50. That is, each segment 60 may be pivotally fixed to the central core 50. Thus, each segment 60 encircles the central core 50, as seen in FIGS. 5 and 7-8. As shown in FIG. 8, each articulation band 44 is located laterally between the lateral walls 66 of the segments 60 and the central core 50. The lateral distance between the central core 50 and a lateral wall 66 may be substantially the same as, or slightly greater than, the lateral thickness of the corresponding articulation band 44. In this way, each segment 60 laterally constrains the corresponding articulation band 44. That is, as described in greater detail below, as the articulation region 10 bends, the segments 60 restrain the articulation bands 44 laterally to prevent their motion substantially away from the central core 50.

Figure 9:
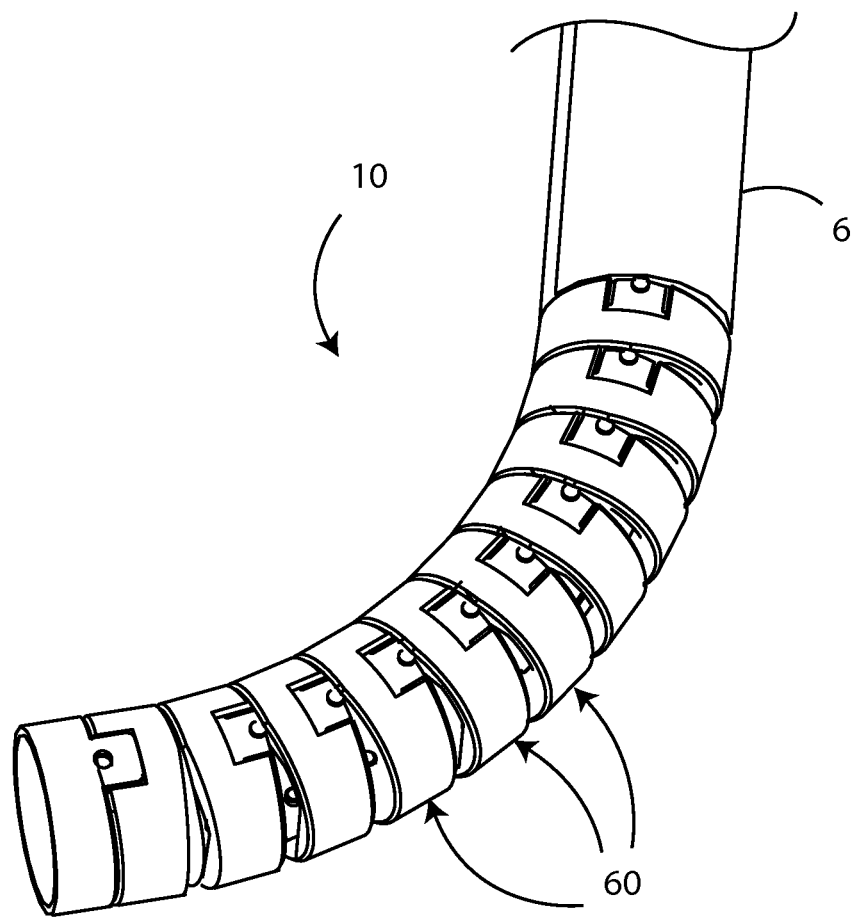
FIG. 9 is a perspective view of the articulation region of FIG. 6, in an articulated configuration.

The segments 60 advantageously do not substantially contact one another in a neutral state in which the articulation region 10 is substantially straight, as seen in FIG. 6. That is, the segments 60 are not connected to one another, affirmatively or otherwise, and instead are disconnected from one another. In this way, the segments 60 substantially do not carry an axial load, which is a load oriented longitudinally along the articulation region 10. Instead, the articulation bands 44 and/or central core 50 carry substantially all of the axial load through the articulation region 10. One of the lateral edges of a segment 60 may contact the lateral edge of another segment 60 when the articulation region 10 is curved, where such contact limits the amount of articulation of the articulation region as seen in FIG. 9. However, even in this fully-bent configuration the segments 60 substantially do not carry an axial load.

Operation

The user possesses the surgical instrument 2. The end effector 4 is placed in the body in proximity to its desired location relative to tissue. Advantageously, the end effector 4 is advanced through a trocar port or other minimally-invasive opening into the body. Where the end effector 4 includes a staple holder 30 and anvil 32, the end effector 4 may be opened such that at least the distal end of the anvil 32 is spaced apart from the staple holder 30 to allow tissue to be placed therebetween. However, the end effector 4 may be any other implement for treating tissue.

At least one articulation band 44 is then manipulated to cause the articulation region 10 to bend. As one example, one articulation band 44 may be refracted proximally toward the handle 8. Simultaneously, the other articulation band 44 may be allowed to move distally away from the handle 8, or may be affirmatively pushed distally. Each articulation band 44 is fixed to the end effector 4 as set forth above, such as by affixation relative to a pin 46 or other structure of the end effector 4. Thus, as the proximal force exerted on one articulation band 44 acts to pull that articulation band 44 proximally, it pulls the corresponding pin 46 proximally. However, the central core 50 is positioned between the end effector 4 and the portion of the shaft 6 proximal to the articulation region 10 that is substantially rigid, substantially preventing the end effector 4 as a whole from moving proximally under the effect of that proximal force. Instead, that proximal force exerted on a pin 46 on the end effector 4 that is located lateral to the longitudinal centerline of the shaft 6 causes a moment that bends the articulation region 10 laterally toward the side of the end effector 4 from which the pin 46 extends to which proximal force is applied by an articulation band 44. As the articulation region 10 bends laterally, the articulation band 44 tends to pull away from the central core 50. However, the lateral walls 66 adjacent to the articulation band 44 that is moving proximally hold the articulation band 44 against or close to the central core 50, because the segments 60 allow little or no room for the articulation band 44 to move laterally relative to the central core 50. In this way, the segments 60 laterally constrain that articulation band 44 against the central core 50. Similarly, the other articulation band 44 that is moved or allowed to move distally tends to move laterally against the central core 50. The other lateral walls 66 of the segments 60 ensure that the other articulation band 44 that moves or is allowed to move distally is held against the central core 50 as well. Consequently, the articulation bands 44 slide along predictable and known paths relative to the central core 50. The articulation region 10 thus bends smoothly as seen in FIG. 9, and the end effector 4 is moved laterally to a desired position relative to the shaft 6 by proximal motion of one of the articulation bands 44. Because the segments 60 are disconnected from one another, and because the inner surfaces of the segments 60 constrain the articulation bands 44 against the central core 50, the segments 60 experience greater hoop stress than axial stress.

The bending of the articulation region 10 relative to the shaft 6 to change the orientation of the end effector 4 is referred to as "articulating" the end effector 4. Once the end effector 4 is in the desired position, the end effector 4 may be closed if it is open, such as by moving the anvil 32 toward the staple holder 30 to clamp tissue. The end effector 4 then may be actuated to treat tissue. Afterwards, the end effector 4 may be reoriented in the manner described above, articulating the end effector 4 in a different direction, so the end effector 4 may treat tissue again. Alternately, the end effector 4 is simply withdrawn from the patient after the first tissue treatment.

The operation of the surgical instrument 2 may be carried out in the course of testing at a factory or other location. If so, the user that possesses the surgical instrument 2 may be a technician, machine or text fixture that exercizes the surgical instrument 2 in the course of testing. The term "tissue," in the context of testing the surgical instrument 2 only, includes any substance or material used as a substitute for tissue in the course of testing.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. The use of terms such as "upward" and "downward" in this document refers to the orientation of parts on the page for descriptive clarity, and in no way limits the orientation of the device in use. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical apparatus, comprising:
a shaft defining a lumen therein;
a plurality of articulation bands extending through and slidable generally longitudinally within said lumen of said shaft;
an end effector affixed to said articulation bands;
a plurality of generally annular segments positioned about said articulation bands along at least a portion of the length of said articulation bands to define an articulated region, wherein said segments laterally constrain said articulation bands, and wherein each of said segments includes a unitary body having a single aperture through which the plurality of articulation bands extends; and
a central core extending from said end effector to said articulated region, wherein said central core is flexible, and wherein at least one said segment is pivotally fixed to said central core.

2. The surgical apparatus of claim 1, wherein said shaft is longitudinally spaced apart from said end effector.

3. The surgical apparatus of claim 1, further comprising a handle connected to the proximal end of said shaft, wherein said articulation bands extend proximally to connect to said handle.

4. The surgical apparatus of claim 1, wherein said segments are attached to a central core via pins.

5. The surgical apparatus of claim 1, further comprising at least one feeder belt, and further comprising a plurality of staples integral with and frangibly separable from said feeder belt.

6. The surgical apparatus of claim 1, wherein each of said segments is rigid.

7. The surgical apparatus of claim 1, wherein said segments are arranged longitudinally sequentially, and wherein adjacent said segments are out of contact from one another in one orientation.

8. The surgical apparatus of claim 1, wherein said segments are fabricated from a plastic material.

9. The surgical apparatus of claim 1, wherein at least one said segment has an interior aperture defined in part by two substantially-vertical and laterally-spaced walls.

10. A surgical apparatus, comprising:
a shaft defining a lumen therein;
a plurality of articulation bands extending through and slidable generally longitudinally within said lumen of said shaft;
an end effector affixed to said articulation bands, wherein said end effector is a surgical stapler;
a feeder belt extending into said end effector;
a plurality of staples integral with and frangibly separable from said feeder belt;
a plurality of generally annular segments positioned about said articulation bands along at least a portion of the length of said articulation bands to define an articulated region, wherein said segments laterally constrain said articulation bands, and wherein each of said segments pivots about a pin; and
a central core extending from said end effector to said articulated region, wherein at least one said segment has an interior aperture defined in part by two substantially-vertical and laterally-spaced walls, and wherein one of said articulation bands is positioned between, and longitudinally slidable between, said central core and a corresponding said wall of at least one said segment wherein each said lateral wall urges a corresponding said articulation belt against said central core.

11. The surgical apparatus of claim 10, wherein said feeder belt extends from said end effector.

12. The surgical apparatus of claim 10, wherein one said lateral wall of at least one said segment is laterally spaced from said central core a distance substantially equal to the lateral thickness of said one of said articulation bands.

13. The surgical apparatus of claim 10, wherein at least one said segment is pivotable about, and longitudinally fixed to said central core about, a vertical axis.

14. The surgical apparatus of claim 10, wherein, during articulation of said articulated region, at least one said segment experiences greater hoop stress than axial stress.

* * * * *